(12) United States Patent
Sundberg et al.

(10) Patent No.: US 7,364,916 B2
(45) Date of Patent: *Apr. 29, 2008

(54) MICROFABRICATED STRUCTURES FOR FACILITATING FLUID INTRODUCTION INTO MICROFLUIDIC DEVICES

(76) Inventors: Steven A. Sundberg, 125 Merced Ave, San Francisco, CA (US) 94127; J. Wallace Parce, 754 Los Robles Ave., Palo Alto, CA (US) 94304; Calvin Y. H. Chow, 455 Minoca Rd., Portola Valley, CA (US) 94028

(*) Notice: Subject to any disclaimer, the term of this patent is extended or adjusted under 35 U.S.C. 154(b) by 0 days.

This patent is subject to a terminal disclaimer.

(21) Appl. No.: 11/617,809

(22) Filed: Dec. 29, 2006

(65) Prior Publication Data

US 2007/0110633 A1   May 17, 2007

Related U.S. Application Data

(60) Continuation of application No. 10/208,297, filed on Jul. 30, 2002, now Pat. No. 7,259,020, which is a division of application No. 09/539,671, filed on Mar. 30, 2000, now Pat. No. 6,451,188, which is a division of application No. 08/870,944, filed on Jun. 6, 1997, now Pat. No. 6,090,251.

(51) Int. Cl.
  *G01N 1/10* (2006.01)
  *B01L 3/02* (2006.01)
(52) U.S. Cl. .................. 436/180; 422/99; 422/100
(58) Field of Classification Search ................. 422/99, 422/100, 102; 436/174, 180
See application file for complete search history.

(56) References Cited

U.S. PATENT DOCUMENTS 3,799,742 A   3/1974   Coleman (Continued)

FOREIGN PATENT DOCUMENTS

WO   94/05414   3/1994

(Continued)

OTHER PUBLICATIONS

Dasgupta, P.K. et al., "Electroosmosis: A Reliable Fluid Propulsion System for Flow Injection Analysis," Anal. Chem. (1994) 66:1792-1798.

(Continued)

*Primary Examiner*—Maureen M. Wallenhorst
(74) *Attorney, Agent, or Firm*—Harness Dickey & Pierce P.L.C.

(57) ABSTRACT

Fluid introduction is facilitated through the use of a port which extends entirely through a microfluidic substrate. Capillary forces can be used to retain the fluid within the port, and a series of samples or other fluids may be introduced through a single port by sequentially blowing the fluid out through the substrate and replacing the removed fluid with an alternate fluid, or by displacing the fluid in part with additional fluid. In another aspect, microfluidic substrates have channels which varying in cross-sectional dimension so that capillary action spreads a fluid only within a limited portion of the channel network. In yet another aspect, the introduction ports may include a multiplicity of very small channels leading from the port to a fluid channel, so as to filter out particles or other contaminants which might otherwise block the channel at the junction between the channel and the introduction port.

12 Claims, 4 Drawing Sheets

U.S. PATENT DOCUMENTS

| | | | |
|---|---|---|---|
| 4,225,410 A | 9/1980 | Pace | |
| 4,426,451 A | 1/1984 | Columbus | |
| 4,517,089 A | 5/1985 | Arnaud | |
| 4,654,127 A | 3/1987 | Baker et al. | |
| 4,686,041 A | 8/1987 | Van den Berg et al. | |
| 4,726,900 A | 2/1988 | Keskinen et al. | |
| 4,795,560 A | 1/1989 | Chupka et al. | |
| 4,908,112 A | 3/1990 | Pace | |
| 4,963,498 A | 10/1990 | Hillman et al. | |
| 4,978,503 A | 12/1990 | Shanks et al. | |
| 5,108,704 A | 4/1992 | Bowers et al. | |
| 5,147,606 A | 9/1992 | Charlton et al. | |
| 5,180,480 A | 1/1993 | Manz | |
| 5,250,263 A | 10/1993 | Manz | |
| 5,262,128 A | 11/1993 | Leighton et al. | |
| 5,296,375 A | 3/1994 | Kricka et al. | |
| 5,304,487 A | 4/1994 | Wilding et al. | |
| 5,376,252 A | 12/1994 | Ekstrom et al. | |
| 5,427,663 A | 6/1995 | Austin et al. | |
| 5,427,946 A | 6/1995 | Kricka et al. | |
| 5,429,734 A | 7/1995 | Gojar et al. | |
| 5,443,890 A | 8/1995 | Ohman | |
| 5,482,608 A | 1/1996 | Keely et al. | |
| 5,486,335 A | 1/1996 | Wilding et al. | |
| 5,500,071 A | 3/1996 | Kaltenbach et al. | |
| 5,503,803 A | 4/1996 | Brown | |
| 5,513,757 A | 5/1996 | Papetti | |
| 5,560,811 A | 10/1996 | Briggs et al. | |
| 5,571,410 A | 11/1996 | Swedberg et al. | |
| 5,603,351 A | 2/1997 | Cherukuri et al. | |
| 5,635,358 A | 6/1997 | Wilding et al. | |
| 5,756,050 A | 5/1998 | Ershow et al. | |
| 5,766,193 A | 6/1998 | Millner | |
| 5,770,029 A | 6/1998 | Nelson et al. | |
| 5,792,354 A | 8/1998 | Aksberg | |
| 5,880,071 A * | 3/1999 | Parce et al. | 204/453 |
| 5,882,930 A | 3/1999 | Baier | |
| 5,885,470 A | 3/1999 | Parce et al. | |
| 5,904,824 A | 5/1999 | Oh | |
| 6,086,825 A * | 7/2000 | Sundberg et al. | 422/100 |
| 6,090,251 A * | 7/2000 | Sundberg et al. | 204/453 |
| 6,143,496 A | 11/2000 | Brown et al. | |
| 6,391,559 B1 | 5/2002 | Brown et al. | |
| 6,451,188 B1 * | 9/2002 | Sundberg et al. | 204/453 |
| 6,709,559 B2 * | 3/2004 | Sundberg et al. | 204/604 |
| 2002/0164820 A1 | 11/2002 | Brown | |
| 2004/0171055 A1 | 9/2004 | Brown | |

FOREIGN PATENT DOCUMENTS

| | | |
|---|---|---|
| WO | 0 620 432 | 10/1994 |
| WO | 96/04547 | 2/1996 |
| WO | 0 725 267 | 8/1996 |
| WO | 96/29595 | 9/1996 |
| WO | 97/02357 | 1/1997 |
| WO | 98/10277 | 3/1998 |
| WO | 98/20020 | 5/1998 |
| WO | 99/34920 | 7/1999 |

OTHER PUBLICATIONS

Effenhauser, C.S. et al., "Glass Chips for High-Speed Capillary Electrophoresis Separations with Submicrometer Plate Heights," Anal. Chem. (1993) 65:2637-2642.

Effenhauser, C.S. et al., "High-Speed Separation of Antisense Oligonucleotides in a Micromachined Capillary Electrophoresis Device," Anal. Chem. (1994) 66:2949-2953.

Fan, Z.H. et al., "Micromachining of Capillary Electrophoresis Injectors and Separators on Glass Chips and Evaluation of Flow at Capillary Intersections," Anal. Chem. (1994) 66:177-184.

Gandhi, "Lithographic Processes," VLSI Fabrication Principles (1983) Chapter 10.

Harrison, D.J. et al., "Capillary Electrophoresis and Sample Injection Systems Integrated on a Planar Glass Chip," Anal. Chem. (1992) 1926-1932.

Harrison, D.J. et al., "Micromachining a Miniaturized Capillary Electrophoresis-Based Chemical Analysis Systems on a Chip," Science (1993) 261:895-897.

Jacobson, S.C. et al., "Effects of Injection Schemes and Column Geometry on the Performance of Microchip Electrophoresis Devices," (1994) 66:1107-1113.

Jacobson, S.C. et al., "High-Speed Separations on a Microchip," (1994) 66:1114-1118.

Jacobson, S.C. et al., "Open Channel Electrochromatography on a Microchip," Anal. Chem. (1994) 66:2369-2373.

Jacobson, S.C. et al., "Precolumn Reactions with Electrophoretic Analysis Integrated on a Microchip," Anal. Chem. (1994) 66:4127-4132.

Jacobson, S.C. et al., "Fused Quartz Substrates for Microchip Electrophoresis," Anal. Chem. (1995) 67:2059-2063.

Khrapko, K. et al., "Mutational Spectrometry Without Phenotypic Selection: Human Mitochondrial DNA," Nucl. Acids Res. (1997) 25(4):685-693.

Kjellin, K.G. et al., "Isotachophoresis of CSF Proteins in Gel Tubes Especially Gammaglobulins," J. Neurol. (1979) 221:225-233.

Linhares, M.C. et al., "Use of an On-Column Fracture in Capillary Zone Electrophoresis for Sample Introduction," Anal. Chem. (1991) 63:2076-2078.

Manz, A. et al., "Miniaturized Total Chemical Analysis Systems: a Novel Concept for Chemical Sensing," Sensors and Actuators (1990) B1:244-248.

Manz, A. et al., "Micromachining of Monocrystalline Silicon and Glass for Chemical Analysis Systems," Anal. Chem. (1991) 10(5):144-149.

Manz, A. et al., "Planar Chips Technology for Miniaturization and Integration of Separation Techniques into Monitoring Systems," J. Chrom. (1992) 593-253-258.

Manz, A., et al., "Electroosmotic pumping and electrophoretic separations for miniaturized chemical analysis systems," J. Micromech. Microeng. (1994) 4:257-265.

Ramsey, J.M. et al., "Microfabricated chemical measurement systems," Nature Med. (1995) 1:1093-1096.

Sandoval, J.E. et al., "Method for the Accelerated Measurement of Electroosmosis in Chemically Modified Tubes for Capillary Electrophoresis," Anal. Chem. (1996) 68:2771-2775.

Seiler, K. et al., "Planar Glass Chips for Capillary Electrophoresis: Repetitive Sample Injection, Quantitation, and Separation Efficiency," Anal. Chem. (1993) 65:1481-1488.

Seiler, K. et al., "Electroosmotic Pumping and Valveless Control of Fluid Flow Within a Manifold of Capillaries on a Glass Chip," Anal. Chem. (1994) 66:3485-3491.

Svendson, P.J. et al., "Separation of Proteins Using Ampholine Carrier Ampholytes as Buffer and Spacer Ions in an Isotachophoresis System," Science Tools, The LKB Instrument Journal (1970) 17(1): 13-17.

Wooley, A.T. et al., "Ultra-high-speed DNA fragment separations using Microfabricated capillary array electrophoresis chips," PNAS (1994) 91:11348-11352.

* cited by examiner

PRIOR ART

FIG. 9

MICROFABRICATED STRUCTURES FOR FACILITATING FLUID INTRODUCTION INTO MICROFLUIDIC DEVICES

CROSS-REFERENCE TO RELATED APPLICATIONS

This application is a continuation of U.S. patent application Ser. No. 10/208,297 filed on Jul. 30, 2002, now U.S. Pat. No. 7,259,020, which is a divisional of U.S. patent application Ser. No. 09/539,671 filed on Mar. 30, 2000, now U.S. Pat. No. 6,451,188, issued Sep. 17, 2002 which is a divisional of U.S. patent application Ser. No. 08/870,944 filed on Jun. 6, 1997, now U.S. Pat. No. 6,090,251 issued Jul. 18, 2000, The disclosures of the above applications are incorporated herein by reference.

BACKGROUND OF THE INVENTION

The present invention relates generally to microfluidic systems and devices and methods for their use. More particularly, the present invention provides structures and methods which facilitate the introduction of fluids into devices having microfluidic channels.

Considerable work is now underway to develop "microfluidic" systems, particularly for performing chemical, clinical, and environmental analysis of chemical and biological specimens. The term microfluidic refers to a system or device having a network of chambers connected by channels, in which the channels have mesoscale dimensions, e.g., having at least one cross-sectional dimension in the range from about 0.1 µm to about 500 µm. Microfluidic substrates are often fabricated using photolithography, wet chemical etching, and other techniques similar to those employed in the semiconductor industry. The resulting devices can be used to perform a variety of sophisticated chemical and biological analytical techniques.

Microfluidic analytical systems have a number of advantages over conventional chemical or physical laboratory techniques. For example, microfluidic systems are particularly well adapted for analyzing small sample sizes, typically making use of samples on the order of nanoliters and even picoliters. The substrates may be produced at relatively low cost, and the channels can be arranged to perform numerous specific analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures. Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

Unfortunately, work in connection with the present invention has found that the structures and methods used to introduce samples and other fluids into microfluidic substrates can limit the capabilities of known microfluidic systems. Fluid introduction ports provide an interface between the surrounding world and the microfluidic channel network. The total number of samples and other fluids which can be processed on a microfluidic substrate is now limited by the size and/or the number of ports through which these fluids are introduced to the microfluidic system. Known structures and methods for introduction of fluids into microfluidic systems also generally result in the transfer of a much greater volume of fluid than is needed for microfluidic analysis.

Work in connection with the present invention has also identified unexpected failure modes associated with known methods for introducing fluids to microfluidic channels. These failure modes may result in less than desirable overall reliability for microfluidic systems. Finally, a need has been identified for some mechanism to accurately pre-position different fluids within a contiguous microfluidic network, so as to facilitate a variety of microfluidic analyses.

It would therefore be desirable to provide improved structures, systems, and methods which overcome or substantially mitigate at least some of the problems set forth above. In particular, it would be desirable to provide microfluidic systems which facilitated the transfer of small volumes of fluids to an introduction port of a microfluidic substrate, and to increase the number of fluids which can be manipulated within the substrate without increasing the overall size of the substrate itself. It would be particularly desirable to provide microfluidic introduction ports which could accept multiple fluid samples, and which were less prone to failure than known introduction port structures. Finally, it would be advantageous to provide microfluidic channel networks which are adapted to controllably pre-position differing liquids within adjoining channels for analysis of samples using differing fluid media.

SUMMARY OF THE INVENTION

The present invention overcomes at least some of the deficiencies of known structures and methods for introducing fluids into microfluidic substrates. In some embodiments, fluid introduction can be facilitated through the use of a port which extends entirely through the substrate structure. Capillary forces can be used to retain the fluid within such a through-hole port, rather than relying on gravity to hold the fluid within a cup-like blind hole. A series of samples or other fluids may be introduced through a single through-hole port by sequentially blowing the fluid out of the port, and replacing the removed fluid with different fluid. Advantageously, an array of such through-hole ports can wick fluids from the surfaces of a corresponding array of pins, thereby avoiding the need for complex pipette systems. In another aspect, the present invention provides microfluidic substrates having channels which vary in cross-sectional dimension so that capillary action spreads a fluid only within a limited portion of the channel network. In yet another aspect, the introduction ports of the present invention may include a multiplicity of very small channels leading from the port to a larger microfluidic fluid channel. These small channels filter out particles or other contaminants which might otherwise block the microfluidic channel.

In a first aspect, the present invention provides a microfluidic system comprising a substrate having an upper surface, a lower surface, and a microfluidic channel disposed between these surfaces. A wall of the substrate borders a port for receiving fluid. The port is in fluid communication with the channel, and the port is open at both the upper surface of the substrate, and at the lower surface of the substrate.

Generally, the port has a cross-sectional dimension which is sufficiently small so that capillary forces restrain the fluid within the port. The specific size of the port will depend in part on the properties of the material along its border. The capillary forces between the port and the fluid can also be used to transfer the fluid from the outer surface of a pin, rather than relying on a complex pipette system. The use of a through-hole port also facilitates the removal of the fluid from the port, as the fluid can be blown through the substrate with differential pressure, or simply displaced from the port with an alternate fluid. Optionally, the lower surface of the substrate may have a hydrophobic material to prevent the sample from spreading along the lower surface, while a hydrophilic rod or capillary tube may facilitate decanting of the fluid from the port.

In another aspect, the present invention provides a method for introducing a fluid into a microfluidic channel of a substrate. The method comprises transporting the fluid from outside the substrate to a port of the substrate through a first surface. The port extends through the substrate, and opens on a second surface of the substrate. The microfluidic channel of the substrate is in fluid communication with the port between the first and second surfaces. The fluid is restrained within the port at least in part by a capillary force between the port and the fluid.

In yet another aspect, the present invention provides a method for introducing a plurality of samples into a microfluidic substrate. The method comprises forming a volume of each sample on an associated pin. The pins are arranged in an array, and the array of pins is aligned with an array of ports on the substrate. The aligned pins and ports are brought together so that the volumes transfer from the pins to associated ports of the substrate.

In yet another aspect, the present invention provides a method for introducing a plurality of fluids into a microfluidic substrate. The method comprises inserting a first fluid into a port of the substrate. A portion of the first fluid is transferred from the port into a microfluidic channel of the substrate. An unused portion of the first fluid is removed from the port, and a second fluid is inserted into the port.

The present invention also provides a microfluidic system comprising a body having a first channel and a capillary limit region. A second channel is in fluid communication with the first channel through the limit region. The second channel has a cross-sectional dimension adjacent the limit region which is larger than a cross-sectional dimension of the limit region. This difference in cross-sectional dimensions inhibits wicking from the limit region into the second channel.

Generally, a minimum cross-sectional dimension of the limit region is sufficiently smaller than a minimum cross-sectional dimension of the second channel so that differential capillary forces prevent wicking of fluid from the first channel, through the limit region, and into the second channel when there is no fluid in the second channel. Typically, the first channel and limit region end at the intersection with the second channel, while the second channel continues on past the intersection (like the top bar in a "T"). This structure is particularly advantageous to establish predetermined boundaries between two different fluids within a microfluidic channel network, as a fluid which is introduced into the first channel will wick through the channel to the limit region, but will not wick beyond the limit region into the second channel. A second different fluid can then wick through the second channel, beyond the intersection with the first limit region, thereby defining a boundary between the first and second fluids at the channel intersection.

In another aspect, the present invention provides a method for controllably distributing fluids within microfluidic substrates. The method comprises wicking a first fluid along a first channel and into a capillary limit region. The first fluid is prevented from wicking beyond the limit region and into a second channel by differential capillary force.

The present invention also provides a filtered microfluidic system comprising a substrate having a reservoir and a channel having a fluid microfluidic cross-section. A plurality of filter channels extend in parallel between the reservoir and the channel. Each filter channel has a cross-sectional dimension which is smaller than a fluid channel cross-sectional dimension of the microfluidic channel.

In yet another aspect, the present invention provides a method for filtering a fluid sample entering a microfluidic channel network. The method comprises introducing the fluid sample into a port, and passing the fluid sample through a plurality of filter channels which are arranged in parallel. The filter channels block particles having cross-sections which are larger than a maximum filter particle size. The filtered fluid sample is collected and transported through a microfluidic channel having a cross-section which is larger than the maximum filter size.

DESCRIPTION OF THE SPECIFIC EMBODIMENTS

Figure 1:
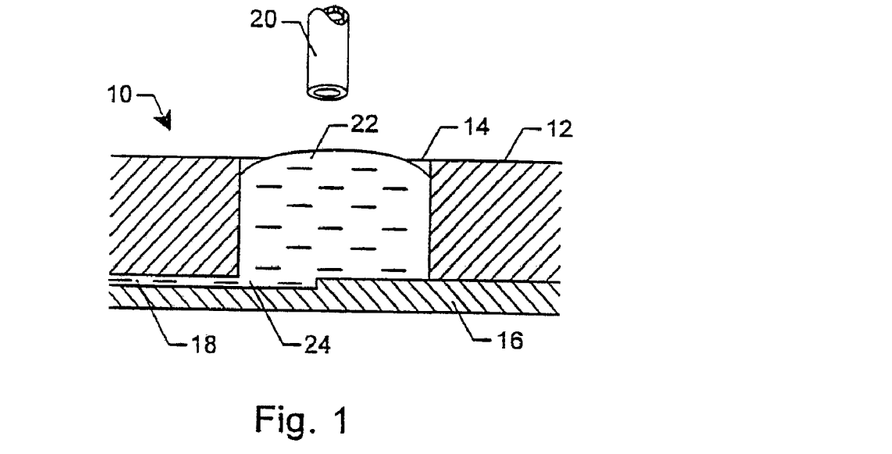
FIG. 1 is a cross-sectional view of a typical microfluidic fluid introduction system, in which a pipette deposits fluid in a blind hole, and in which the fluid must pass through a single microfluidic channel to enter the channel network.

A typical microfluidic introduction system and method is schematically illustrated in FIG. 1. A substrate 10 generally comprises an upper portion 12 through which a port 14 has been drilled. A lower portion 16 is bonded to upper portion 12, the lower portion having a microfluidic channel 18 which is in fluid communication with port 14. A pipette 20 delivers fluid 22 to port 14, typically relying on pneumatic and/or hydraulic pressure to deposit the fluid in the port.

Work in connection with the present invention has identified failure modes which could prevent fluid 22 from reaching channel 18, thereby interfering with the intended operation of microfluidic substrate 10. In the first failure mode, any particles in the fluid, in the pipette, or in the port may flow with the fluid from the port toward channel 18. Particles which are not large enough to enter microfluidic channel 18 will be deposited at channel entrance 24, thereby blocking flow from the port to the channel. As microfluidic channels get smaller and smaller, there is a corresponding increase in sensitivity to even minute particles of contamination blocking the entrance 24 to port 18.

In another failure mode for typical microfluidic structures, the drops deposited by pipette 20 into port 14 may include bubbles, or air (or other gases) may be trapped within the port below the drop of fluid. Where an air bubble covers entrance 24 to port 18, the fluid will not enter the channel through capillary wicking.

As the advantages of microfluidic structures are generally enhanced by decreasing the size of the system components, it is generally desirable to decrease the size of port 14. For example, this allows the fabrication of microfluidic systems having larger numbers of fluid ports on a substrate of a given size. This would allow each substrate to simultaneously analyze larger numbers of samples, or may alternatively allow more complex chemical or biochemical analyses to be performed. Regardless, as the size of port 14 decreases, the likelihood that a bubble will be trapped under the fluid increases. In fact, port 14 may eventually be made small enough that fluid remains over the upper surface of the substrate without substantially entering port 14.

Figure 2:
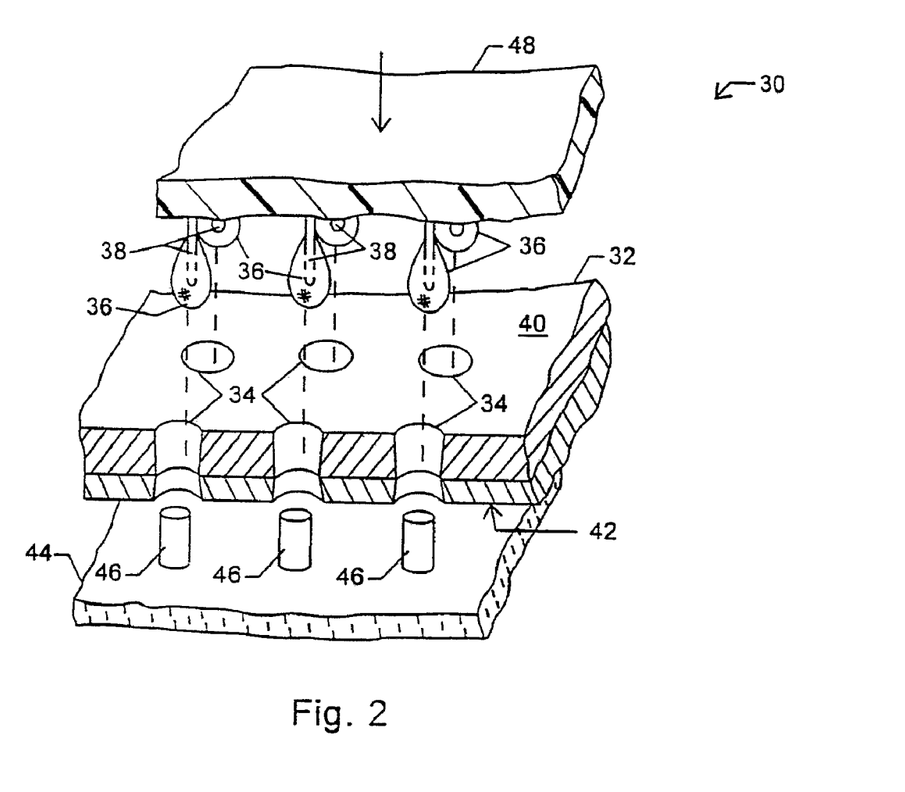
FIG. 2 is a perspective view in partial cross-section showing a system for introducing an array of fluid samples to a corresponding array of through-hole ports, and also shows the use of hydrophilic rods to facilitate decanting the fluid samples from the through-hole ports, according to the principles of the present invention.

To overcome these failure modes and disadvantages, microfluidic fluid introduction system 30 includes a microfluidic substrate 32 having an array of throughhole ports 34, as illustrated in FIG. 2. Samples and other fluids are transferred into through-hole ports 34 as drops 36 on the outer surfaces of a corresponding array of pins 38. Surprisingly, through-hole ports 34 extend entirely through substrate 32 from an upper surface 40 to a lower surface 42. Drops 36 will wick into through-hole ports 34, and will be restrained within the through-hole ports by capillary forces between the fluid and the surrounding ports. A fluid removal system 44 includes rods 46 which facilitate decanting the fluid from the through-hole ports, as will be described in more detail hereinbelow.

Pins 38 are mounted on a pin support structure 48. As pins 38 are aligned with through-hole ports 34, a large number of individual drops 36 may be transferred simultaneously from the pins to the through-hole ports by moving pin support structure 48 into close proximity with substrate 32. Drops 36 may be formed on pins 38 by dipping the pins in an associated array of fluid receptacles, by distributing the fluid through channels within fluid support structure 48, or the like. As only very small amounts of fluid are needed for the microfluidic analysis, the size of drops 36 can be quite small. By relying on pins to transfer drops on their outer surfaces (rather than individual pipettes with complex hydraulic or pneumatic systems), the cost and complexity of a system for transporting a large number of discrete drops of fluid into associated microfluidic ports can be substantially reduced. The pins may optionally be aligned in an array corresponding to at least a portion of a standard microtiter plate, e.g.,. 12 rows of 8 pins on 9 mm spacings, to facilitate preparing samples and other fluids with conventional chemical and biological techniques.

As drops 36 enter through-hole ports 34, they are drawn into the ports by both gravity and capillary forces. As through-hole ports 34 extend entirely through substrate 40, no air can be trapped between the drops and the bottom of the port. As the through-hole ports rely on capillary forces to retain the fluid, it should be noted that the orientation of the port can be changed from vertical to horizontal, angled, etc., so that the terms "upper surface" and "lower surface" are relative to an arbitrary orientation of the substrate. Nonetheless, an at least partially vertical orientation may be preferred to facilitate transferring drops 36 on pins 38 to through-hole ports 34.

Generally, capillary forces draw fluids from larger channels to smaller channels. More specifically, capillary forces are largely controlled by the minimum cross-sectional dimension of a channel. For example, capillary forces will wick a fluid from a channel having a width of 100 micrometers and a depth of 20 micrometers into a contiguous channel having a width of 100 micrometers and a depth of 10 micrometers. Hence, simple capillary forces may optionally be relied on to draw fluid from throughhole port 34 into microfluidic channels within substrate 32 (not shown in FIG. 2), so long as the microfluidic channels have a smaller cross-sectional dimension than the smallest cross-sectional dimension of the through-hole ports. Additional or alternative mechanisms are also available for injecting fluid from the through-hole ports into the microfluidic channels of the substrate, including electrokinetics, differential pneumatic pressure, and the like.

Figure 3:
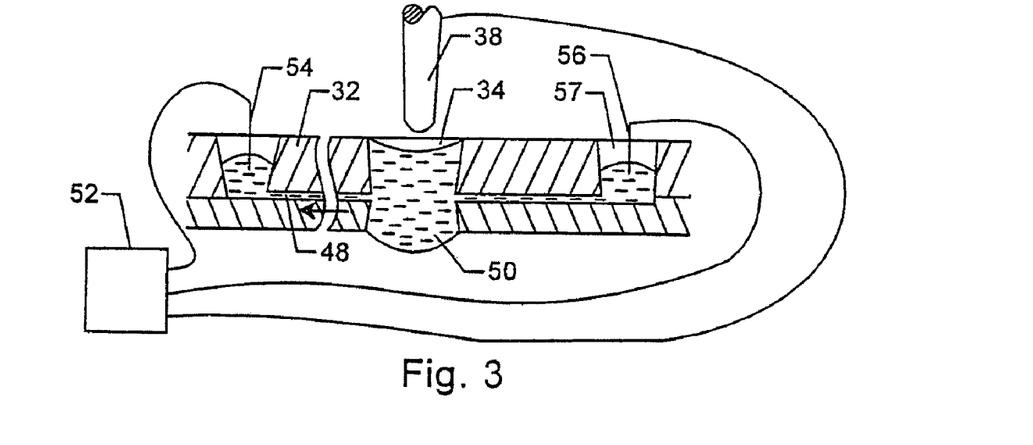
FIG. 3 is a cross-sectional view illustrating the use of capillary forces to retain a fluid sample within a through-hole port, and also illustrates the use of electrokinetic forces to transport the fluid within the microfluidic substrate.

As can be understood with reference to FIG. 3, application of an electrical current, potential, or charge between microfluidic channel 48 and a fluid 50 within through-hole port 34 can help inject the fluid into the channel. Typically, an electrical power source 52 will be coupled to a waste fluid reservoir electrode 54, and to a port electrode 56 (and/or pin 38). Port electrode 56 is coupled to fluid 50 through an electrical access port 57. The port access electrode and waste port electrode may be formed as conductors which extend downward into their associated ports from pin support structure 48, or from a separate electrical connector assembly, so that no electrodes need be incorporated into substrate 32. As used therein, the term port encompasses the structure of a microfluid substrate which allows access to the microfluidic channels for introducing fluids and other materials, and/or for electrically coupling electrodes to the fluid within the channels. The term reservoir encompasses ports and other structures of the substrate which accommodate a significantly greater volume of fluid than the microfluidic channels. The use of electrokinetics as a transportation mechanism within microfluidic channels is more fully described in U.S. Pat. No. 5,880,071, issued on Mar. 9, 1999, and in Published PCT Application No. WO 96/04547, the full disclosures of which are incorporated herein by reference. Similar transportation mechanisms may facilitate transfer of the fluid from the outer surface of pin 38 to through-hole port 34 by the application of an electrical field through the pin and port electrode 56. Alternatively, the through- hole ports of the present invention are also well suited for use with standard pipette systems.

Useful substrate materials include glass, quartz and silicon, as well as polymeric substrates, e.g., plastics. In the ease of polymeric substrates, the substrate materials may be rigid, semi-rigid, or non-rigid, opaque, semi-opaque or transparent, depending upon the use for which they are intended. For example, devices which include an optical or visual detection element, will generally be fabricated, at least in part, from transparent materials to allow, or at least facilitate that detection. Alternatively, transparent windows of, e.g., glass or quartz, may be incorporated into the device for these types of detection elements. Additionally, the polymeric materials may have linear or branched backbones, and may be crosslinked or non-crosslinked. Examples of particularly preferred polymeric materials include, e.g., polymethylmethacrylate (PMMA) polydimethylsiloxanes (PDMS), polyurethane, polyvinylchloride (PVC), polystyrene, polysulfone, polycarbonate, and the like.

The cross-sectional dimensions of through-hole port 34 will typically be selected to provide sufficient capillary force between fluid 50 and the port to at least help restrain the fluid within the port. Preferably, the cross-section will have a minimum diameter which is sufficient to induce a capillary force which will overcome the force of gravity (which pulls fluid 50 through the open bottom of the through-hole port). The specific minimum cross-sectional dimensions of through-hole port 34 which will provide this capillary force will depend on the wettability of the material bordering the port, the fluid to be retained therein, the distance between the channel and the bottom of the substrate if the through-hole port has a vertical orientation, and the like. For example, through-hole ports in many plastic materials will be smaller than similar through-hole port structures in glass substrates, due to the higher wettability of glass.

Through-hole ports 34 will typically be drilled through substrate 32 with a circular cross-section, the cross-section of the through-hole port typically having a diameter of between about 0.1 mm and 5 mm, and ideally having a diameter within the range of from about 0.5 mm to 2 mm. Such holes may be drilled using "air abrasion", an erosion process which is similar to a precisely directed sandblast of the substrate material. Air abrasion services are commercially available from NYS Enterprises of Palo Alto, Calif. Alternatively, ultrasonic drilling or laser photoablation may be used to provide quite small ports through the substrate. In other embodiments, small carbide drill bits may mechanically drill thorough the substrate to provide through-hole ports having small enough cross-sectional dimensions to induce the desired capillary forces. Through-hole ports may also be formed during the substrate molding or embossing processes, particularly when the substrates comprise polymeric materials.

While the structures are here illustrated as having slightly tapering cross-sections, they may alternatively have constant diameters, or may decrease near one or both surfaces. The holes may be drilled through the entire substrate in one operation, or may alternatively be drilled independently through separate upper and lower portions of the substrate prior to bonding these portions together. The cross-section of the through-hole ports need not be the same through the upper and lower portions, and should be tolerant of some mismatch between the location and size of the openings formed in the upper and lower portions of the substrate. A wide variety of alternative port cross-sectional shapes may also be used, with the diameter ranges given above generally defining the minimum cross-sectional dimension. For example rectangular (or any other arbitrary shape) ports may be formed in at least one portion of the substrate structure while the channels are formed by etching a fenestration through the substrate portion.

Regardless of the specific cross-section, the through-hole ports will preferably have a total volume between the upper and lower surfaces of substrate of less than about 20 µl, ideally having a volume of between about 0.5 µl and 10 µl. As the through-hole ports of the present invention generally facilitate the use of smaller sample volumes, they are particularly advantageous for use in drug discovery application, such as those described in U.S. Patent No. 6,046,056, full disclosure of which is incorporated herein by reference.

Figure 4:
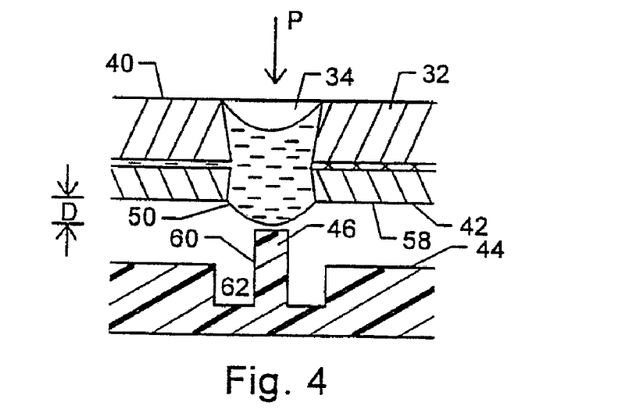
FIG. 4 is a cross-sectional view showing the use of differential pressure and a hydrophilic rod to decant a sample from a through-hole port.

Referring now to FIG. 4, a particular advantage of through-hole ports 34 is that they facilitate the introduction of multiple fluids into a microfluidic network using a single port structure. Fluid 50 may be removed from through-hole port 34 by applying a differential gas pressure P over the top of substrate 32 (relative to the pressure below the substrate), effectively blowing the fluid out through the through-hole port. Optionally, rods 46 decant fluid 50 from the through-hole port when the pressure extends the fluid more than a distance D beyond lower surface 42. A hydrophobic coating 58 (e.g., a polytetrafluoroethylene such as Teflon™) helps prevent smearing of fluid 50 over lower surface 42 of substrate 32, thereby avoiding cross-contamination of fluid samples. Decanting may be enhanced by a hydrophilic coating 60 on the surface of rod 46, or alternatively by using decanting structures which have a capillary channel. Fluid removed from through-hole port 34 is collected in well 62, and the wells may optionally be connected by drains to a fluid disposal system.

While differential pressure is a particularly advantageous mechanism for simultaneously removing fluids from multiple through-hole ports in a substrate, the present invention also encompasses other mechanisms for simultaneously or individually removing the samples, including electrokinetically distending the sample from lower surface 42 (as can be understood with reference to FIG. 3), displacing fluid 50 with an alternate fluid introduced into ports 34 through upper surface 40 (using a pipette, pins 38, or the like), inserting decanting structures into ports 34, and the like. In general, fluid 50 may be directly replaced by an alternate fluid for use in the fluidic network, or a cleaning or neutral solution may first be entered into through-hole port 34 to minimize cross-contamination of the sequentially introduced fluids. Regardless, the ability to sequentially introduce multiple fluids into a microfluidic network through a single port substantially enhances the effectiveness of that port as an interface between the microfluidic network and the surrounding world.

Figure 5:
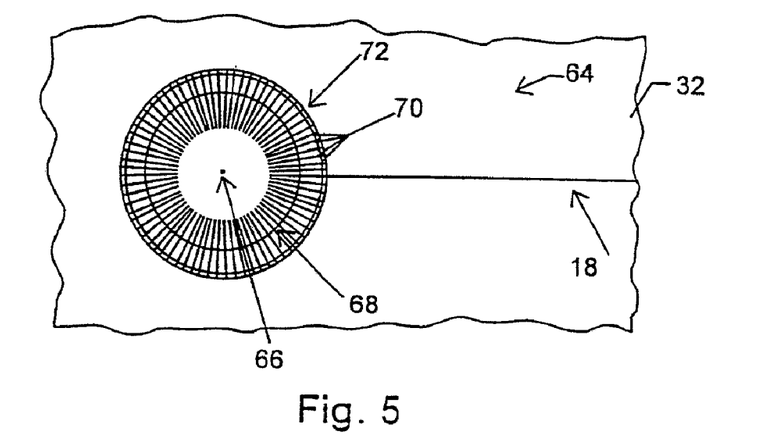
FIG. 5 is a plan view of an integrated reservoir and filter to prevent particles from blocking the microfluidic channels of the substrate.
Figure 6:
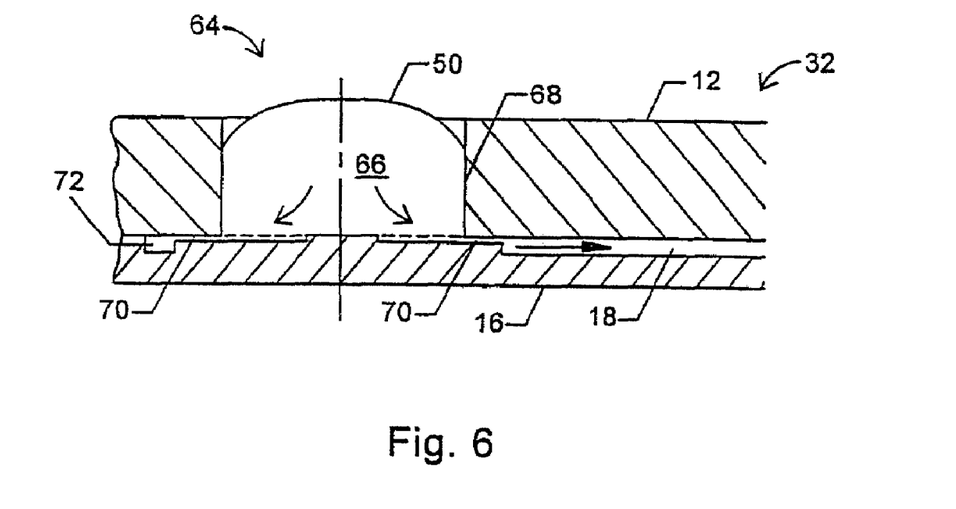
FIG. 6 is a cross-sectional view showing the integrated port and filter of FIG. 5.

Referring now to FIGS. 5 and 6, a filtered port 64 in substrate 32 is illustrated with a blind reservoir 66, but may alternatively be used with the through-hole port structure described hereinabove. Reservoir 66 is defined by a hole 68 drilled through upper portion 12 of substrate 32, while a microfluidic channel 18 has been imposed on lower portion 16. To prevent particles from blocking the entry to channel 18, a multiplicity of radial filter channels 70 lead from reservoir 66. Filter channels 70 transmit fluid from reservoir 66 to a header channel 72, which in turn opens to channel 18. However, particles larger than some maximum filter particle size (which will vary with the cross-section of the filter channel) will be left in the port. This prevents large particles from blocking channel 18.

Filter channel 70 has at least one smaller cross-sectional dimension than channel 18, the filter channel often being smaller in cross-sectional area than channel 18. Preferably, the filter channels 70 are individually sufficiently small to block entry of particulates which might impede flow through channel 18. However, there are a sufficient number of functionally parallel filter channels so that the sum of the cross-sectional areas of all the filter channels together is at least as large as channel 18, ideally being substantially larger than channel 18 to minimize head loss through the filter structure. In fact, as filter channels 70 may individually be blocked by particulates, the sum of the cross-sectional areas of the filter channels will determine the filter capacity. In other words, the more total cross-sectional area of filter channels, the more particulate matter the filter can remove from the flow before the filter becomes blocked. Hence, the total cross-sectional area of all the filter channels together will preferably be in the range from about 2 to about 100 times larger than the cross-section of channel 18. Header channel 72 will typically be about the same size as channel 18.

Channel 18 will typically have a minimum cross-sectional dimension of between about 0.5 and 100 µm. Filter channels 70 will generally be smaller than fluid channel 18, ideally having a minimum cross-sectional dimension of between about 10 and 50% of the minimum cross-sectional dimension of channel 18. There will generally be between about 10 and 100 functionally parallel filter channels. Typical channel dimensions are about 10 micrometers deep and 70 micrometers wide for channel 18 and header channel 72, while the corresponding filter channels will typically be about 2 micrometers deep and 10 micrometers wide.

A wide variety of reservoir, filter channel, and header channel geometries might be used to prevent blockage of fluids as they enter fluid channel 18. For example, filter channels 70 may extend geometrically parallel to each other from one side of reservoir 68 to a straight header channel normal to fluid channel 18. However, the radial filter geometry illustrated in FIG. 5 is preferred, as it minimizes the substrate surface area consumed by the filter.

Figure 7:
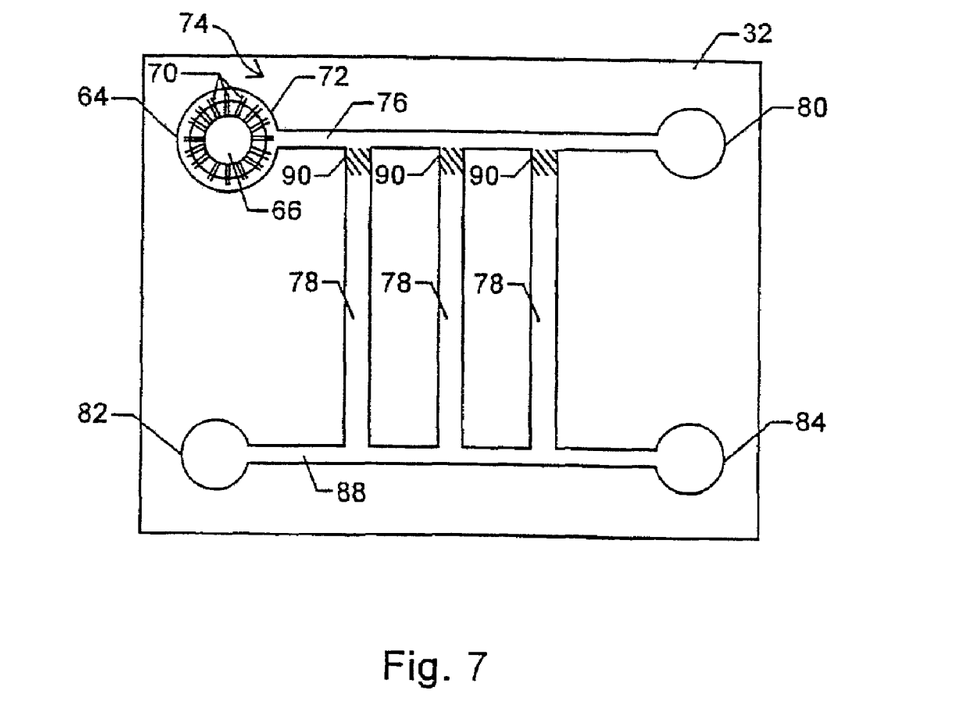
FIG. 7 schematically illustrates a microfluidic substrate having fluid stops which allow two different fluids to be positioned within the network, with the boundaries between the fluids being located at predetermined limit regions.
Figure 8:
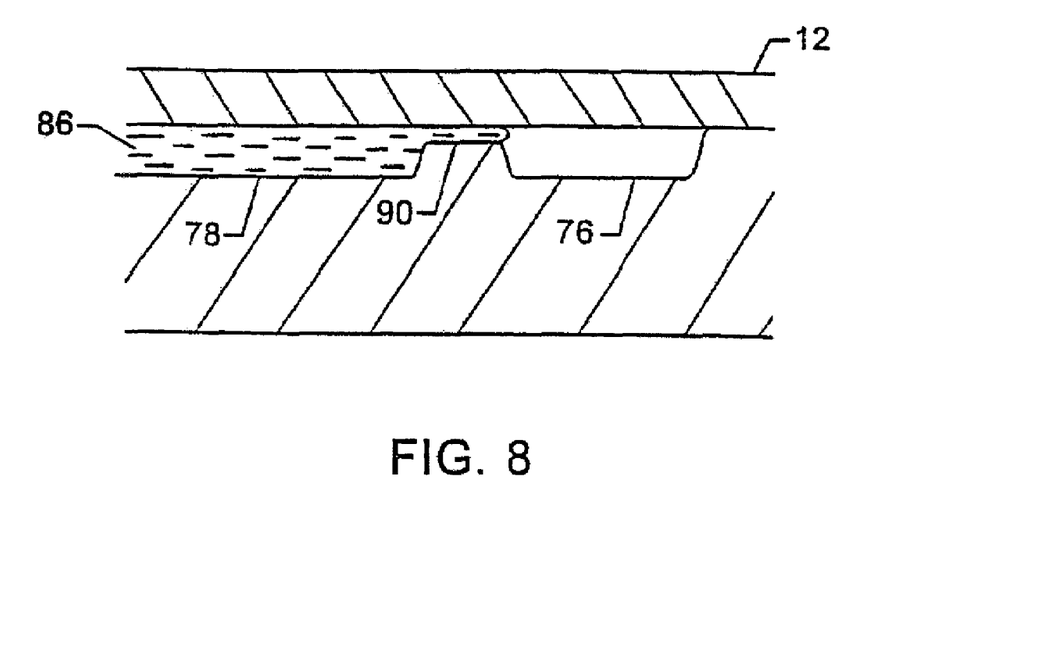
FIGS. 8 and 9 are cross-sectional views showing the structure and operation of the fluid stop limit regions of FIG. 7.
Figure 9:
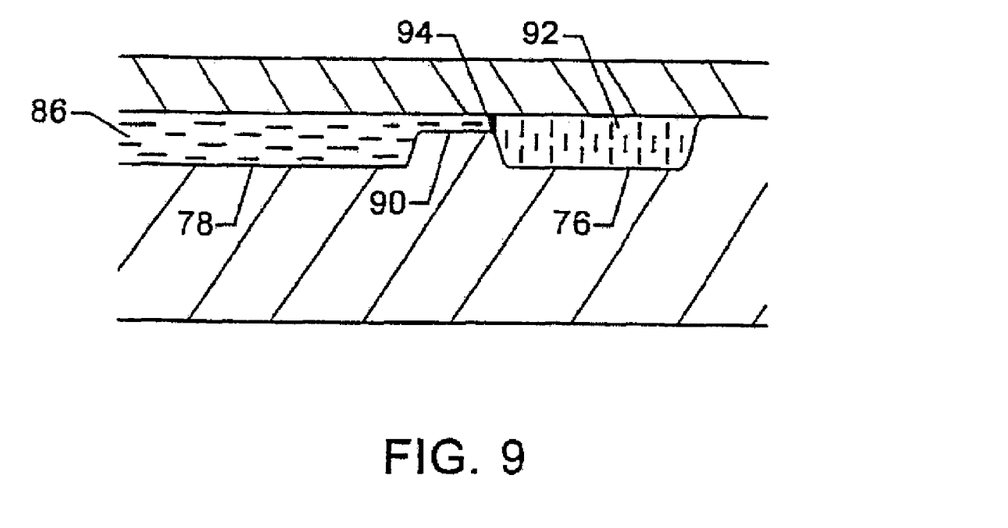

Referring now to FIGS. 7-9, it will be useful in many microfluidic networks to pre-position different fluids within a microfluidic network at predetermined locations. For example, a microfluidic channel network 74 includes an electroosmotic channel 76 from which three electrophoretic separation channels 78 extend. Electrophoretic channels 78 will preferably contain a separation solution including a polymer, while electroosmotic channel 76 will preferably be filled with a buffer solution to facilitate transportation of a fluid sample from filtered reservoir 64. Unfortunately, if all of the channels have uniform cross-sections, any fluid introduced into any of the reservoirs 64, 80, 82, or 84, will wick throughout channel network 74.

To limit the capillary wicking of a first solution 86 to electrophoretic channels 78, the first solution is introduced into one of the adjoining reservoirs 82, 84. First solution 78, which will be an electrophoretic polymer containing solution in our example, will wick along a cross-channel 88 and into each of electrophoretic channels 78. Furthermore, the first solution will wick along each of the electrophoretic channels toward electroosmotic channel 76. The air displaced from within the electrophoretic channels can escape through electroosmotic channel, and out through the adjoining ports.

To prevent the first fluid from filling the electroosmotic channel 76, a limit region 90 is disposed adjacent the junction of the two types of channels. Limit region 90 will have at least one cross-sectional dimension which is smaller than a cross-sectional dimension of the adjacent electroosmotic channel 76, the limit region ideally having a narrowest cross-sectional dimension which is smaller than the narrowest cross-sectional dimension of the electroosmotic channel. As a result, the first fluid will wick in to the limit region from electrophoretic channel 78, but differential capillary forces will prevent first fluid 86 from passing through limit region 90 and wicking into electroosmotic channel 76. The ratio of the minimum cross-sectional dimensions may again vary with the properties of the materials bordering the limit region and channels, with the limit region generally having a minimum dimension of less than 90% that of the channel. Typical electroosmotic and electrophoretic channel dimensions will be about 70 µm wide by 10 µm deep, while the corresponding limit regions may be about 70 µm wide by about 2 µm deep.

A second fluid 92 introduced at reservoir 80 will wick through electroosmotic channel 76 past limit regions 90, thereby defining an interfluid boundary 94 substantially disposed at the interface between limit region 90 and electroosmotic channel 76. It should be noted that electroosmotic channel extends across limit regions 90 (rather than having a dead end at the limit region) to avoid trapping air between first fluid 86 and second fluid 92. As a result, the air within electroosmotic channel 76 is free to leave the opening provided at filtered reservoir 64, so that all of the channels of channel network 74 are substantially filled with fluid. Although this example has been described in terms of "electrophoretic" and "electroosmotic" channels, it will be appreciated that the present invention can be used in any application where it may be desirable to place different fluids within intersecting channel structures.

It should also be noted that second fluid 92, will wick into header channel 72 so long as the header channel is not significantly larger in its narrowest cross-sectional dimension than electroosmotic channel 76. Additionally, the buffer solution will proceed into the small filter channels 70 from header channel 72. However, the buffer solution will generally not advance beyond filter channels 70 into reservoir 66, as the filter channels effectively provide limit regions between the reservoir and the header channel. To prevent this "limit region" effect of the filter channels from inhibiting flow from the reservoir into the adjacent channel system, it will generally be preferable to introduce some fluid into the header and filter channels prior to introducing a fluid directly into reservoir 66. Similarly, fluid channel networks having a plurality of fluid introduction ports will generally include at least one unfiltered port structure. Otherwise, it might be difficult to advance any fluid into the network beyond the small filter channels surrounding each port.

While the exemplary embodiments of the present invention have been described in some detail, by way of illustration and for clarity of understanding, a number of modifications, adaptations, and alternative embodiments will be obvious to those of skill in the art. For example, the present invention may be used with microfluidic structures that rely on pneumatic pressure or a vacuum to move materials within microfluidic channels. Therefore, the scope of the present invention is limited solely by the appended claims.

What is claimed is:

1. A method of retaining fluid for analysis, the method comprising:
   retaining a first test fluid in a first through-hole port in a substrate by solely inducing capillary forces in said first fluid with said first through-hole port;
   retaining a second test fluid in a second through-hole port in said substrate by solely inducing capillary forces in said second fluid with said second through-hole port; and
   inhibiting cross-contamination between said first test fluid in said first through-hole port and said second test fluid in said second through-hole port with a hydrophobic coating along a surface of said substrate.

2. The method according to claim 1, further comprising: transporting said first test fluid from outside said substrate to said first through-hole port.

3. The method according to claim 2 wherein said transporting said first test fluid from outside said substrate to said first through-hole port comprises retaining said first test fluid upon an exterior of a pin member and depositing said first test fluid in said first through-hole port.

4. The method according to claim 2 wherein said transporting said first test fluid from outside said substrate to said first through-hole port comprises retaining said first test fluid within a pipette and depositing said first test fluid in said first through-hole port.

5. The method according to claim 1 wherein said inhibiting cross-contamination with a hydrophobic coating along said surface of said substrate comprises inhibiting cross-contamination with a hydrophobic coating along a surface of said substrate adjacent an exit end of said first through-hole port.

6. The method according to claim 1, wherein said inhibiting cross-contamination with a hydrophobic coating along said surface of said substrate comprises inhibiting cross-contamination with a hydrophobic coating along a surface of said substrate adjacent an entrance end of said first through-hole port.

7. A method of retaining fluid for analysis, the method comprising:
retaining a first test fluid in a first through-hole port in a substrate by solely inducing capillary forces in said first fluid with said first through-hole port;
retaining a second test fluid in a second through-hole port in said substrate by solely inducing capillary forces in said second fluid with said second through-hole port; and
inhibiting flow of said first test fluid or said second test fluid between said first through-hole port and said second through-hole port using a hydrophobic coating disposed on said substrate.

8. The method according to claim 7, further comprising:
transporting said first test fluid from outside said substrate to said first through-hole port.

9. The method according to claim 8 wherein said transporting said first test fluid from outside said substrate to said first through-hole port comprises retaining said first test fluid upon an exterior of a pin member and depositing said first test fluid in said first through-hole port.

10. The method according to claim 8 wherein said transporting said first test fluid from outside said substrate to said first through-hole port comprises retaining said first test fluid within a pipette and depositing said first test fluid in said first through-hole port.

11. The method according to claim 7 wherein said inhibiting flow using said hydrophobic coating disposed on said substrate comprises inhibiting flow using a hydrophobic coating disposed along a surface of said substrate adjacent an exit end of said first through-hole port.

12. The method according to claim 7 wherein said inhibiting flow using said hydrophobic coating disposed on said substrate comprises inhibiting flow using a hydrophobic coating disposed along a surface of said substrate adjacent an entrance end of said first through-hole port.

* * * * *